US009348322B2

(12) United States Patent
Fraser et al.

(10) Patent No.: US 9,348,322 B2
(45) Date of Patent: May 24, 2016

(54) SMART DEVICE INCLUDING BIOMETRIC SENSOR

(71) Applicant: Google Technology Holdings LLC, Mountain View, CA (US)

(72) Inventors: Nicholas A. Fraser, Grayslake, IL (US); Chad E. Davis, Chicago, IL (US); Thomas E. Gitzinger, Libertyvill, IL (US); Dickon Isaacs, Chicago, IL (US); Mitul R. Patel, Lake Zurich, IL (US)

(73) Assignee: Google Technology Holdings LLC, Mountain View, CA (US)

( * ) Notice: Subject to any disclaimer, the term of this patent is extended or adjusted under 35 U.S.C. 154(b) by 94 days.

(21) Appl. No.: 14/462,759

(22) Filed: Aug. 19, 2014

(65) Prior Publication Data

US 2015/0355604 A1    Dec. 10, 2015

Related U.S. Application Data

(60) Provisional application No. 62/007,967, filed on Jun. 5, 2014.

(51) Int. Cl.
| | |
|---|---|
| *G01N 33/48* | (2006.01) |
| *G04G 21/02* | (2010.01) |
| *H04B 5/00* | (2006.01) |
| *H02J 7/02* | (2016.01) |
| *G01J 1/04* | (2006.01) |
| *A61B 5/1455* | (2006.01) |
| *A61B 5/024* | (2006.01) |

(52) U.S. Cl.
CPC .......... *G04G 21/025* (2013.01); *A61B 5/02416* (2013.01); *A61B 5/02438* (2013.01); *A61B 5/14551* (2013.01); *G01J 1/0407* (2013.01); *H02J 7/025* (2013.01); *H04B 5/0031* (2013.01)

(58) Field of Classification Search
CPC ....................................................... G01N 33/48
USPC ............................................................ 356/39
See application file for complete search history.

(56) References Cited

U.S. PATENT DOCUMENTS

| | | | | |
|---|---|---|---|---|
| 5,002,387 | A * | 3/1991 | Baljet .................... | G03B 35/16 348/E13.04 |
| 6,597,438 | B1 * | 7/2003 | Cabuz ................ | G01N 15/1404 356/39 |
| 7,911,617 | B2 * | 3/2011 | Padmanabhan ...... | G01B 11/272 356/246 |
| 2003/0142291 | A1 * | 7/2003 | Padmanabhan ........ | A61B 5/417 356/39 |

OTHER PUBLICATIONS

Mio Global; from http://www.mioglobal.com/Mio-ALPHA-Heart-Rate-SportWatch/product.aspx?productid=13&deptid=1&pricecat=2&gclid=CKThhp2okr0CFcli7AodSmgAPw; printed Jan. 20, 2016.

\* cited by examiner

*Primary Examiner* — Roy M Punnoose
(74) *Attorney, Agent, or Firm* — Faegre Baker Daniels LLP

(57) ABSTRACT

An apparatus can include a wrist worn device configured to be worn on a wrist of a user. The apparatus can include a controller. The apparatus can include a power supply. The apparatus can include a light emitter that can emit light from a user side of the wrist worn device to a wrist of the user. The apparatus can include a light detector that can detect light reflected from the wrist of the user from the first light emitter and can send a detector signal to the controller. The detector signal can be based on the detected light. The apparatus can include a lens coupled to a user side of the wrist worn device external to the light emitter and light detector. The lens can include an opaque section. The lens can also include light transmissive section that transmits light from the light emitter to the user.

20 Claims, 5 Drawing Sheets

SMART DEVICE INCLUDING BIOMETRIC SENSOR

BACKGROUND

1. Field

The present disclosure is directed to a smart device including a biometric sensor.

2. Introduction

Presently, smart watches and smart glasses provide information and an interface for users beyond traditional watches and glasses. For example, a smart watch wirelessly pairs with a cellular phone and provides a user interface for the cellular phone. A smart watch includes a display that displays time information and cellular phone information including text message information and incoming call information. The smart watch also includes a touch screen that receives user input for both the smart watch and a paired cellular phone and includes a microphone for voice communication.

Unfortunately, due to the small real estate of smart watches and smart glasses, they do not provide all of the features desired by users, such as effective biometric sensor features while maintaining a desirably small size. Thus, there is a need for a smart device including an effective biometric sensor.

BRIEF DESCRIPTION OF THE DRAWINGS

In order to describe the manner in which advantages and features of the disclosure can be obtained, a description of the disclosure is rendered by reference to specific embodiments thereof which are illustrated in the appended drawings. These drawings depict only example embodiments of the disclosure and are not therefore to be considered to be limiting of its scope.

DETAILED DESCRIPTION

Embodiments provide an apparatus including a biometric sensor. According to a possible embodiment, the apparatus can be a user portable apparatus. The apparatus can include a wrist worn device configured to be worn on a wrist of a user. The apparatus can include a controller coupled to the wrist worn device. The apparatus can include a power supply coupled to the controller. The apparatus can include a light emitter coupled to the controller. The light emitter can emit light from a user side of the wrist worn device to a wrist of the user. The apparatus can include a light detector coupled to the controller. The light detector can detect light reflected from the wrist of the user from the first light emitter and can send a detector signal to the controller. The detector signal can be based on the detected light. The apparatus can include a lens coupled to a user side of the wrist worn device external to the light emitter and light detector. The lens can include an opaque section. The lens can also include light transmissive section that transmits light from the light emitter to the user.

According to another possible embodiment, the apparatus can include a user worn frame configured to be worn by a user. The apparatus can include a controller coupled to the user worn frame. The apparatus can include a power supply coupled to the controller. The apparatus can include a light emitter coupled to the controller. The light emitter can emit light from a user side of the user worn frame to skin of the user. The apparatus can include a light detector coupled to the controller. The light detector can detect light from the first light emitter reflected from the user. The light detector can send a detector signal to the controller. The detector signal can be based on the detected light. The apparatus can include a lens coupled to a user side of the user worn frame external to the light emitter and light detector. The lens can include an opaque section. The lens can include a first light transmissive section that transmits light from the light emitter to skin of the user. The lens can include a second light transmissive section separate from the first light transmissive section. The second light transmissive section can transmit light reflected from the user to the light detector. The apparatus can include a wireless transceiver configured to transmit and receive a wireless communication signals including signals based on the detector signal generated by the light detector.

Figure 1:
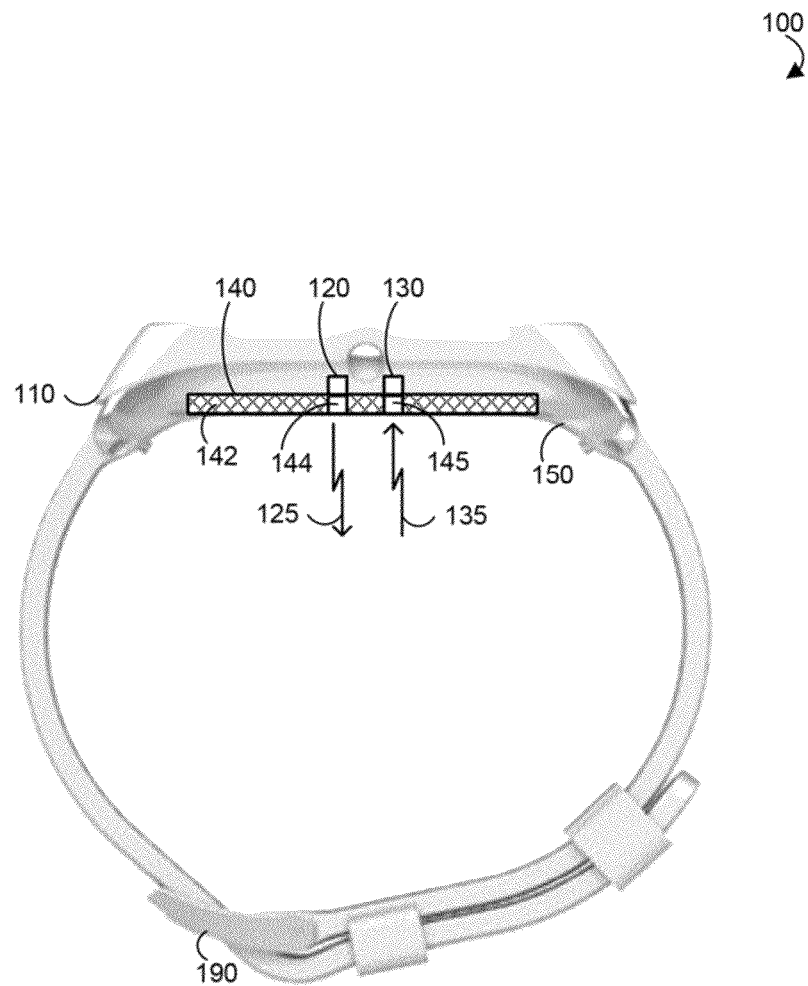
FIG. 1 is an example illustration of a user portable apparatus according to a possible embodiment.

FIG. 1 is an example illustration of a user portable apparatus 100 according to a possible embodiment. The apparatus 100 can be a wrist worn apparatus, a watch, a smart watch, or other types of a wrist worn apparatus. For example, the apparatus 100 also can be a wristband, can be a bracelet, can have a fastener 290, such as a clamp or a buckle, can encircle part or all of the user's wrist, can be flexible, can be rigid, or can be any other device that can be worn on a wrist of a user. According to other embodiments, the device 100 can be smart glasses, a wireless communication earpiece, such as a Bluetooth® headset, or any other smart device that can be worn by a user. For conciseness, embodiments are described with respect to a wrist worn apparatus. However, embodiments can also be applied to smart glasses, wireless headsets, and other user worn devices.

The apparatus 100 can include a wrist worn device 110 configured to be worn on a wrist of a user. The apparatus 100 can include a light emitter 120 that can emit light 125 from a user side 150 of the wrist worn device 110 to a wrist of the user. The light emitter 120 can include one or more of different types of light emitters. For example, the light emitter 120 can include a red light emitter, an infrared light emitter, a green light emitter, a yellow light emitter, a white light emitter, and/or any other light emitter that can be used to detect biometric information of a user. For example, a red light emitter and an infrared light emitter can be used to detect blood oxygen saturation, such as oxygen saturation of hemoglobin in a volume of intravascular blood of the user, heart rate, and other biometric information. Additionally, one, two, or more green light emitters can also be used to detect blood oxygen saturation, heart rate, and/or other biometric information. Furthermore, a combination of red, infrared, and green light emitters can be used to detect blood oxygen saturation, heart rate, and/or other biometric information. For example, red and infrared light emitters can be used to detect blood oxygen saturation and a green light emitter can be used to detect heart rate.

The apparatus 100 can include a light detector 130 that can detect light 135 reflected from the wrist of the user from the first light emitter 120. The light detector 130 can be a photodetector, a light sensor, or any other light detector. The light emitter 120 and light detector 130 can be used for photoplethysmography, pulse oximetry, and other biometric sensing.

The apparatus 100 can include a lens 140 coupled to a user side of the wrist worn device 110 external to the light emitter 120 and the light detector 130. The lens 140 can include an opaque section 142, a first light transmissive section 144. The first light transmissive section 144 can transmit the light 125 emitted from the light emitter 120 to a wrist of the user. The apparatus 100 can also include a second light transmissive section 145 separate from the first light transmissive section 144. The second light transmissive section 145 can transmit light 135 reflected from the wrist of the user to the light detector 130. When multiple light emitters are used, the lens 140 can include multiple separate light transmissive sections for each light emitter and for the detector. For example, each light transmissive section 144 and 145 can be an aperture in the opaque section 142. Furthermore, if multiple light emitters are used, the light transmissive section 145 for the detector 130 can be located in between light transmissive sections for each of the two or more light emitters. The light transmissive sections 144, 145 can be fully transmissive or can be partially transmissive to only transmit light of a desired wavelength through the lens 140.

The lens 140 can have an opaque layer 142 including the light transmissive sections 144 and 145. The lens 140 can also be an opaque lens including the light transmissive sections 144 and 145 as apertures in the lens. The lens 140 can be made of metal, plastic, glass, thermoplastic, such as Poly(methyl methacrylate) (PMMA), or any other useful material. The lens opaque section 142 can be a screen printed layer, a spray painted layer, or other opaque layer. The lens 140 can further include a coated layer, such as a clear coat layer, that provides protection, durability, scratch resistance, and other protection on a user side of the lens 140. The coated layer can be part of the opaque layer 142 or can be separate from the opaque layer 142. The lens 140 can also provide the opaque section 142 by being opaque and the transmissive sections 144 and 145 can be etched, molded, drilled, laser cut, or otherwise formed to provide transmissive sections 144 and 145 in the lens 140. The opaque section 142 can conceal portions of the apparatus 100 from the user to hide internal components of the apparatus 100 from view. The opaque section 142 can include decorations and the decorations can incorporate the light transmissive sections 144 and 145 into the decorations to obscure or highlight the light transmissive sections 144 and 145.

Figure 2:
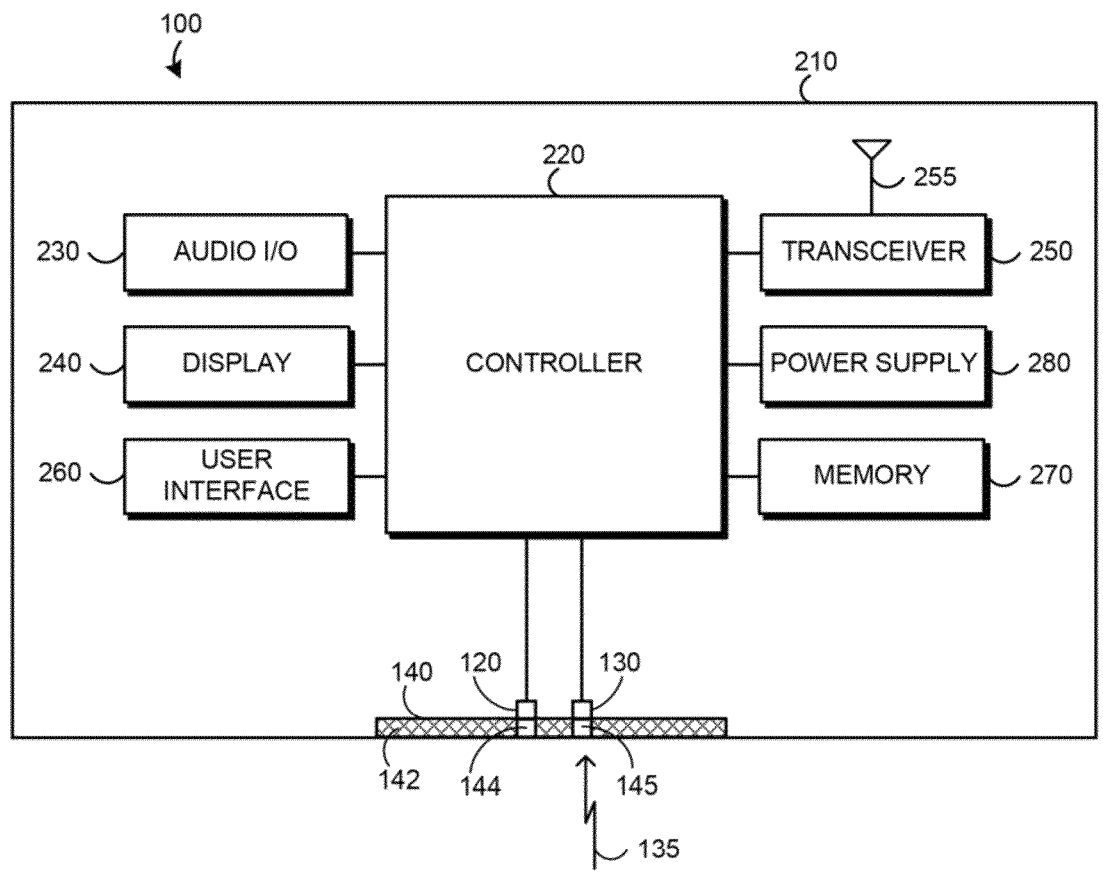
FIG. 2 is an example block diagram of an apparatus according to a possible embodiment.

FIG. 2 is an example block diagram of the apparatus 100 according to a possible embodiment. The apparatus 100 can include the lens 140 having the opaque section 142 and the light transmissive sections 144 and 145. The apparatus 100 can also include the light emitter 120 and the light detector 130. The apparatus 200 can further include a housing 210, a controller 220 within the housing 210, audio input and output circuitry 230 coupled to the controller 220, a display 240 coupled to the controller 220, a transceiver 250 coupled to the controller 220, an antenna 255 coupled to the transceiver 250, a user interface 260 coupled to the controller 220, a memory 270 coupled to the controller 220, and a power supply 280 coupled to the controller 220. The light emitter 120 and light detector 130 can also be coupled to the controller 220. The light detector 130 can send a detector signal to the controller 220, where the detector signal can be based on the detected light 135. The housing 210 can be a housing that houses the components of the apparatus 100. The housing 210 can also be a user worn frame, such as a watch frame, a smart watch frame, a smart glasses frame, a headset frame, or any other user worn frame.

The display 240 can be a touch screen display, a flat screen display, a liquid crystal-based display, a light emitting diode-based display, a flexible display, a head's-up display, an optical head mounted display, a micro projector, and/or any other display. The display 240 can display digital clock information, can display a digital representation of an analog watch face, can display message notices, such as text messages and notices of e-mail messages, can display reminders, can display a strength of a wireless communication signal, can display information received wirelessly from a smart phone, can display other smart watch information, and/or can display other useful information. Furthermore, the controller 220 can send a user biometric signal to the display 240 based on a detector signal from the light detector 130 and the display 240 can display biometric information based on the biometric signal. The biometric information can include heart rate information, pulse oximetry information, blood oxygenation information, such as oxygen saturation (SpO2), and/or other biometric information.

The transceiver 250 may include a wireless transmitter and/or a receiver. The transceiver 250 can include a radio frequency transmitter, a near filed communication transmitter, a wireless local area network transmitter, a cellular network transmitter, an infrared transmitter, and/or any other wireless transmitter. The transceiver 250 can transmit a wireless communication signal based on the detector signal generated by the light detector 130. The wireless communication signal can be a wireless near field communication signal, a wireless local area network communication signal, or a cellular communication signal. The transceiver 250 can also transmit other wireless communication signals, such as communication signals including voice communications, voice commands, user touchscreen input information, and other wireless communication signals.

The audio input and output circuitry 230 can include a microphone, a speaker, a transducer, or any other audio input and output circuitry. The user interface 260 can include a keypad, a keyboard, buttons, a touch pad, a joystick, a touch screen display, another additional display, or any other device useful for providing an interface between a user and an electronic device. The power supply 280 can be a rechargeable battery, a capacitive cell array, a disposable battery, an ultracapacitor, a solar cell, multiple power supplies, or any other portable power supply. The memory 270 can include a random access memory, a read only memory, an optical memory, a subscriber identity module memory, a flash memory, a removable memory, a hard drive, a cache, or any other memory that can be coupled to a wireless communication device.

The apparatus 100 or the controller 220 may implement any operating system, such as Microsoft Windows®, UNIX, or LINUX, Android, or any other operating system. Apparatus operation software may be written in any programming language, such as C, C++, Java or Visual Basic, for example. Apparatus software may also run on an application framework, such as, for example, a Java® framework, a .NET® framework, or any other application framework. The software and/or the operating system may be stored in the memory 270 or elsewhere on the apparatus 200. The apparatus 200 or the controller 220 may also use hardware to implement operations. For example, the controller 220 may be any programmable processor. Disclosed embodiments may also be implemented on a general-purpose or a special purpose computer, a programmed microprocessor, peripheral integrated circuit elements, an application-specific integrated circuit or other integrated circuits, hardware/electronic logic circuits, such as a discrete element circuit, a programmable logic device, such as a programmable logic array, field programmable gate-array, or the like. In general, the controller 220 may be any controller or processor device or devices capable of operating an electronic device and implementing the disclosed embodiments.

Figure 3:
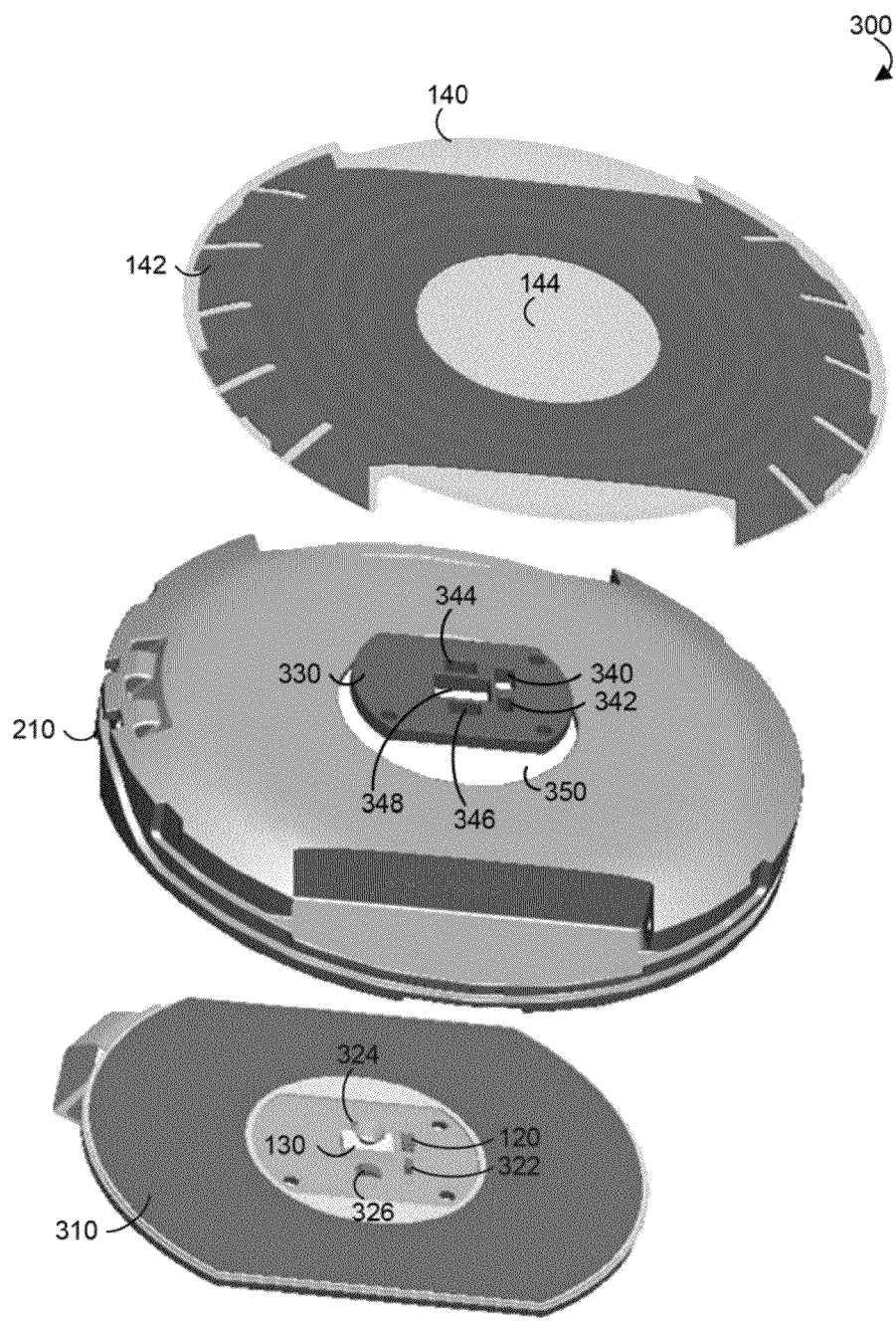
FIG. 3 is an example user side exploded view of an apparatus according to a possible embodiment.

FIG. 3 is an example a user side exploded view of an apparatus 300, such as a user side exploded view of a portion of the apparatus 100, according to a possible embodiment. The apparatus 300 can include the lens 140, the lens opaque section 142, and the lens light transmissive section 144. The apparatus 300 can additionally include the light emitter 120, the light detector 130, and additional light emitters 322, 324, and 326. According to a possible embodiment, the light emitter 120 can be a red light emitter, the light emitter 322 can be an infrared light emitter, and the light emitters 324 and 326 can be green light emitters. The light emitters 120, 322, 324, and 326 can also be other variations of light emitters as discussed above.

The apparatus 300 can also include the housing 210. The housing 210 can include a device aperture 350 on a user side of the apparatus 300 from the light emitters 120, 322, 324, and 326 and the light detector 130. The apparatus 300 can include a grommet 330 within the device aperture 350. The grommet 330 can include a first grommet aperture 340 configured to emit light from the light emitter 120 through the lens light transmissive section 144. The grommet 330 can include a second grommet aperture 348 configured to receive light reflected from the light emitter 120 through the light transmissive section 144 to the light detector 130. The grommet 330 can also include additional grommet apertures 344 and 346 for additional light emitters 324 and 326. For example, the light emitters 324 and 326 can be green light emitters located on opposite sides of the light detector 130. Accordingly, the grommet apertures 344 and 346 for the light emitters 324 and 326 can be located on opposite sides of the grommet aperture 348 for the light detector 130. Other combinations of light emitter 120, 322, 324, and 326, light detector 130, and grommet aperture 340, 342, 344, 346, and 348 locations can also be used. The grommet apertures 340, 342, 344, 346, and 348 and/or separate light transmissive sections 144 of the lens 140 can prevent crosstalk between light emitters 120, 322, 324, and 326 and can prevent crosstalk between the light emitters 120, 322, 324, and 326 and the light detector 130.

The apparatus 300 can include a charging coil 310 surrounding the light emitters 120, 322, 324, and 326 and the light detector 130. The light emitters 120, 322, 324, and 326 and the light detector 130 can be placed in the middle of the charging coil 310 to reduce the thickness of the apparatus 300. The charging coil 310 can charge the power supply 280 shown in FIG. 2. For example, the charging coil can 310 be used for electromagnetic charging, capacitive charging, inductive charging, or other wireless charging of the power supply 280.

Figure 4:
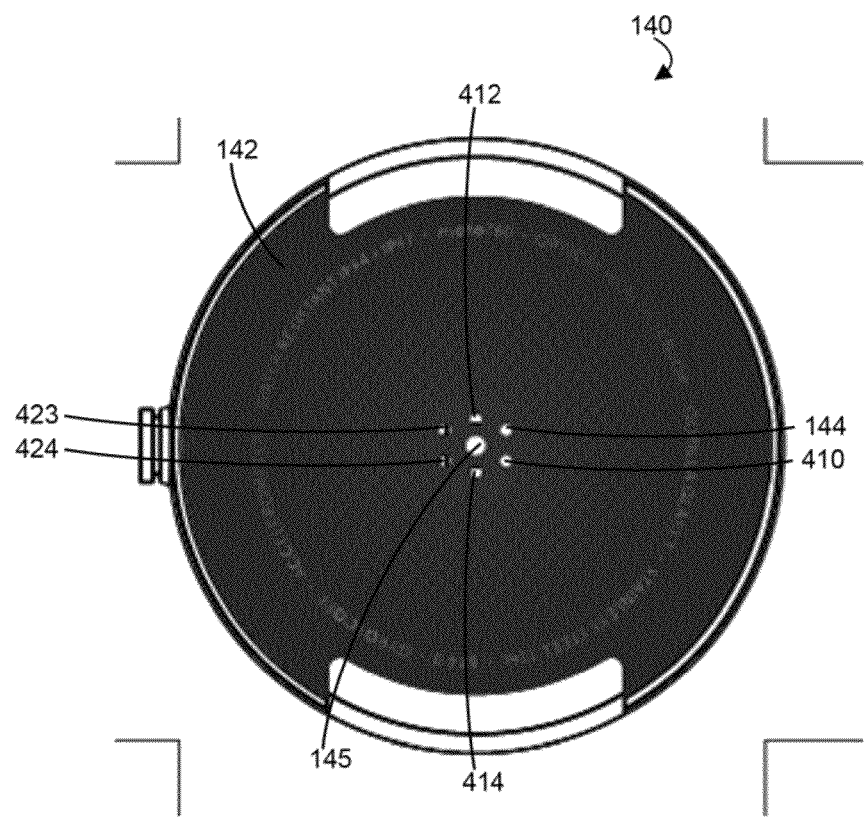
FIG. 4 is an example illustration of a lens according to a possible embodiment.

FIG. 4 is an example illustration of the lens 140 according to a possible embodiment. The lens 140 can include the opaque section 142. The lens 140 can also include a plurality of light transmissive sections 144, 145, 410, 412, 414, 423, and 424. The light transmissive sections 144, 145, 410, 412, 414, 423, and 424 can be separate and distinct from each other in the opaque section 142. The light transmissive sections 144, 410, 412, 414, 423, and 424 can transmit light from the light emitters 120, 322, 324, 326 of FIG. 3 and other light emitters. The light transmissive section 145 can transmit light reflected from a user to the light detector 130 of FIG. 3. Variations of light transmissive sections or apertures can be used. For example, the light transmissive sections 423 and 424 may only be included for aesthetic purposes, such as to provide a pleasing design of light transmissive sections on the lens 140. Also, the light transmissive sections 423 and 424 can be apertures in the lens 140 to provide sound or other functions.

Figure 5:
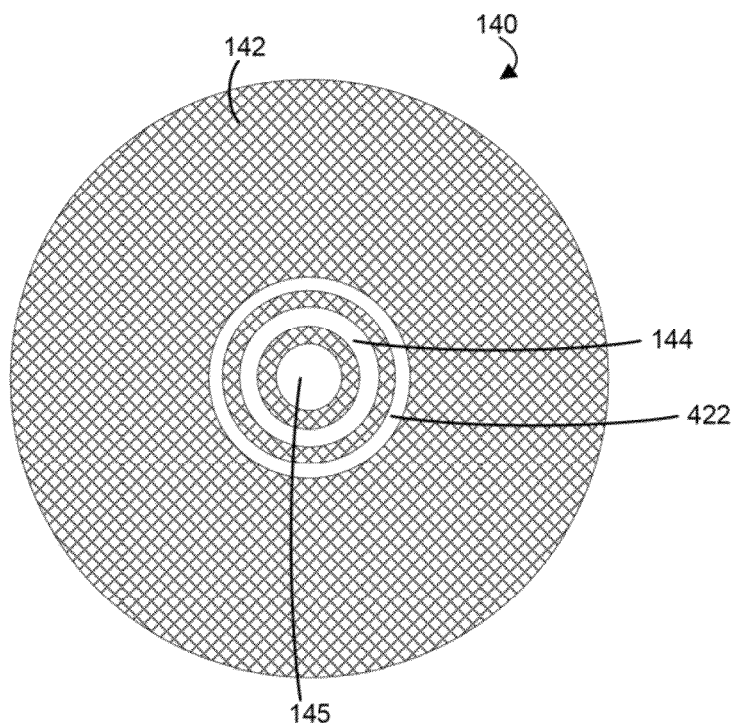
FIG. 5 is an example illustration of a lens according to another possible embodiment.

FIG. 5 is an example illustration of the lens 140 according to another possible embodiment. The lens 140 can include the opaque section 142. The lens 140 can also include light transmissive sections 144, 145, and 422. This embodiment illustrates a possible variation of light transmissive sections. Other designs of light transmissive sections can also be used depending on aesthetics and functionality of the lens 140.

Embodiments can provide a lens and grommet that can cover up components of an apparatus, allow for a seamless design, and allow for apparatus components to be hidden. Embodiments can also provide for a light sealing grommet and artwork on a lens including light transmissive sections to focus emitted and received light.

Operations of this disclosure can be implemented on a programmed processor. However, the controller 220 may also be implemented on a general purpose or special purpose computer, a programmed microprocessor or microcontroller and peripheral integrated circuit elements, an integrated circuit, a hardware electronic or logic circuit such as a discrete element circuit, a programmable logic device, or the like. In general, any device on which resides a finite state machine capable of implementing the flowcharts shown in the figures may be used to implement the processor functions of this disclosure.

While this disclosure has been described with specific embodiments thereof, it is evident that many alternatives, modifications, and variations will be apparent to those skilled in the art. For example, various components of the embodiments may be interchanged, added, or substituted in the other embodiments. Also, all of the elements of each figure are not necessary for operation of the disclosed embodiments. For example, one of ordinary skill in the art of the disclosed embodiments would be enabled to make and use the teachings of the disclosure by simply employing the elements of the independent claims. Accordingly, embodiments of the disclosure as set forth herein are intended to be illustrative, not limiting. Various changes may be made without departing from the spirit and scope of the disclosure.

In this document, relational terms such as "first," "second," and the like may be used solely to distinguish one entity or action from another entity or action without necessarily requiring or implying any actual such relationship or order between such entities or actions. The phrase "at least one of" followed by a list is defined to mean one, some, or all, but not necessarily all of, the elements in the list. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a," "an," or the like does not, without more constraints, preclude the existence of additional identical elements in the process, method, article, or apparatus that comprises the element. Also, the term "another" is defined as at least a second or more. The terms "including," "having," and the like, as used herein, are defined as "comprising." Furthermore, the background section is written as the inventor's own understanding of the context of some embodiments at the time of filing and includes the inventor's own recognition of any problems with existing technologies and/or problems experienced in the inventor's own work.

We claim:

1. A user portable apparatus comprising:
   a wrist worn device configured to be worn on a wrist of a user;
   a controller coupled to the wrist worn device;
   a power supply coupled to the controller;
   a light emitter coupled to the controller, the light emitter configured to emit light from a user side of the wrist worn device to a wrist of the user;
   a light detector coupled to the controller, the light detector configured to detect light reflected from the wrist of the user from the first light emitter, the light detector configured to send a detector signal to the controller, where the detector signal is based on the detected light; and a lens coupled to a user side of the wrist worn device external to the light emitter and the light detector, the lens including an opaque section, and the lens including a light transmissive section that transmits the light emitted from the light emitter to a wrist of the user.

2. The apparatus according to claim 1, wherein the wrist worn device comprises one of a watch and a smart watch.

3. The apparatus according to claim 1,
wherein the light transmissive section comprises a first light transmissive section that transmits light from the light emitter to the wrist of the user, and
wherein the lens includes a second light transmissive section separate from the first light transmissive section, where the second light transmissive section transmits light reflected from the wrist of the user to the light detector.

4. The apparatus according to claim 3,
wherein the lens includes a third light transmissive section separate from the first light transmissive section and the second light transmissive section;
wherein the light emitter comprises:
a first light emitter configured to emit light through the first light transmissive section;
a second light emitter configured to emit light through the third light transmissive section; and
wherein the light detector is configured to detect light emitted from the first light emitter and the second light emitter.

5. The apparatus according to claim 1, further comprising a display coupled to the wrist worn device, the display configured to display at least clock information,
wherein the controller sends a user biometric signal to the display based on the detector signal, and
wherein the display displays biometric information based on the biometric signal.

6. The apparatus according to claim 1, comprising a wireless transmitter configured to transmit a wireless communication signal based on the detector signal generated by the light detector.

7. The apparatus according to claim 3, wherein the wireless communication signal comprises at least one of a wireless near field communication signal, a wireless local area network communication signal, and a cellular communication signal.

8. The apparatus according to claim 1, further comprising a charging coil surrounding the light emitter and the light detector, the charging coil configured to charge the power supply.

9. The apparatus according to claim 1, wherein the wrist worn device comprises:
a device aperture on the user side of the wrist worn device; and
a grommet within the device aperture, the grommet including a first grommet aperture configured to emit light from the light emitter through the lens light transmissive section, and a second grommet aperture configured to receive light reflected from the light emitter to the light detector through the light transmissive section.

10. The apparatus according to claim 1, wherein the lens comprises one of an opaque layer including the light transmissive section and an opaque lens including the light transmissive section as an aperture in the lens.

11. An apparatus comprising:
a user worn frame configured to be worn by a user;
a controller coupled to the user worn frame;
a power supply coupled to the controller;
a light emitter coupled to the controller, the light emitter configured to emit light from a user side of the user worn frame to skin of the user;
a light detector coupled to the controller, the light detector configured to detect light from the first light emitter reflected from the user, the light detector configured to send a detector signal to the controller, where the detector signal is based on the detected light;
a lens coupled to a user side of the user worn frame external to the light emitter and the light detector, the lens including an opaque section, the lens including a first light transmissive section that transmits light from the light emitter to skin of the user, the lens including a second light transmissive section separate from the first light transmissive section, where the second light transmissive section transmits light reflected from the user to the light detector; and
a wireless transceiver configured to transmit and receive a wireless communication signals including signals based on the detector signal generated by the light detector.

12. The apparatus according to claim 11,
wherein the lens includes a third light transmissive section separate from the first light transmissive section and the second light transmissive section;
wherein the light emitter comprises:
a first light emitter configured to emit light through the first light transmissive section;
a second light emitter configured to emit light through the third light transmissive section; and
wherein the light detector is configured to detect light emitted from the first light emitter and the second light emitter.

13. The apparatus according to claim 11, further comprising a display coupled to the user worn frame where the controller sends a user biometric signal to the display based on the detector signal, and where the display displays biometric information based on the biometric signal.

14. The apparatus according to claim 11, further comprising a charging coil surrounding the light emitter and the light detector, the charging coil configured to charge the power supply.

15. The apparatus according to claim 11, further comprising:
a housing coupled to the user worn frame, the housing including the light emitter and the light detector;
a device aperture on the user side of the housing; and
a grommet within the device aperture, the grommet including a first grommet aperture configured to emit light from the light emitter through the light transmissive section, and a second grommet aperture configured to receive light reflected from the light emitter to the light detector through the light transmissive section.

16. The apparatus according to claim 11, wherein the frame comprises one of a smart watch frame, a smart glasses frame, and a wireless communication earpiece frame.

17. An apparatus comprising:
a wrist worn watch configured to be worn on a wrist of a user;
a controller coupled to the wrist worn watch;
a power supply coupled to the controller;
a light emitter coupled to the controller, the light emitter configured to emit light from a user side of the wrist worn watch to a wrist of the user;
a light detector coupled to the controller, the light detector configured to detect light reflected from the wrist of the user from the first light emitter, the light detector configured to send a detector signal to the controller, where the detector signal is based on the detected light;

a lens coupled to a user side of the wrist worn watch external to the light emitter and the light detector, the lens including an opaque section that conceals portions of the wrist worn watch from the user, a first light transmissive section that transmits light from the light emitter to the wrist of the user, and a second light transmissive section separate from the first light transmissive section, where the second light transmissive section transmits light reflected from the wrist of the user to the light detector;

a display coupled to the wrist worn watch, the display configured to display at least clock information, where the controller sends a user biometric signal to the display based on the detector signal, and where the display displays biometric information based on the biometric signal; and a near field radio frequency wireless transceiver configured to transmit a near field radio frequency wireless communication signals including signals based on the detector signal generated by the light detector and configured to receive near field radio frequency wireless communication signals.

18. The apparatus according to claim 17,
wherein the lens includes a third light transmissive section separate from the first light transmissive section and the second light transmissive section;
wherein the light emitter comprises:
a first light emitter configured to emit light through the first light transmissive section;
a second light emitter configured to emit light through the third light transmissive section, and
wherein the light detector is configured to detect light emitted from the first light emitter and the second light emitter.

19. The apparatus according to claim 17, further comprising a charging coil surrounding the light emitter and the light detector, the charging coil configured to charge the power supply.

20. The apparatus according to claim 17, wherein the wrist worn device comprises:
a device aperture on the user side of the wrist worn device; and
a grommet within the device aperture, the grommet including a first grommet aperture configured to emit light from the light emitter through the lens light transmissive section, and a second grommet aperture configured to receive light reflected from the light emitter to the light detector through the light transmissive section.

* * * * *